United States Patent [19]

Cook, II

[11] Patent Number: 5,272,426
[45] Date of Patent: Dec. 21, 1993

[54] CONTROL LOOP FOR MOTORIZED SHUTTER OPERATION

[75] Inventor: James C. Cook, II, 5827 Old U.S. 27 South, Marshall, Mich. 49068

[73] Assignee: James C. Cook

[21] Appl. No.: 670,991

[22] Filed: Mar. 18, 1991

[51] Int. Cl.$^5$ .............................................. G05B 1/06
[52] U.S. Cl. .................................. 318/640; 388/928.1; 388/933
[58] Field of Search ............... 318/640, 254, 615, 619; 388/928.1, 933; 364/413.01, 413.13

[56] References Cited

U.S. PATENT DOCUMENTS

| | | | |
|---|---|---|---|
| 3,580,157 | 5/1971 | Casebeer | 318/640 X |
| 3,605,001 | 9/1971 | Miyakawa | 318/640 X |
| 3,806,789 | 4/1974 | Cap et al. | 318/640 |
| 3,890,550 | 6/1975 | Izumi et al. | 318/640 X |
| 4,072,962 | 2/1978 | Maida | 318/640 X |
| 4,169,990 | 10/1979 | Lerdman | 318/254 X |
| 4,675,586 | 6/1987 | Eigner et al. | 318/458 |
| 4,928,043 | 5/1990 | Plunkett | 318/721 X |
| 5,034,663 | 7/1991 | Cook | 318/308 |

Primary Examiner—William M. Shoop, Jr.
Assistant Examiner—David Martin
Attorney, Agent, or Firm—Price, Heneveld, Cooper, DeWitt & Litton

[57] ABSTRACT

A light system is disclosed for controlling the amount of light supplied from a high density light source to a target. A shutter is positioned between the light source and the target, and a motor is coupled to said shutter to control the position of said shutter. Either manual or automatic control of said shutter is provided by electronic means coupled to said motor.

26 Claims, 10 Drawing Sheets

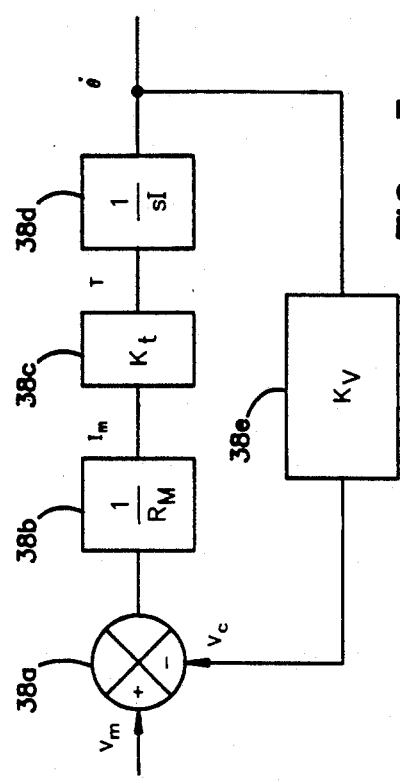
FIG. 3a
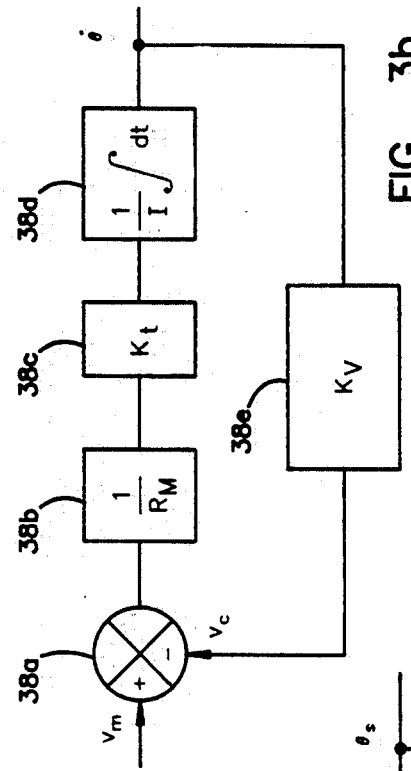
FIG. 3b
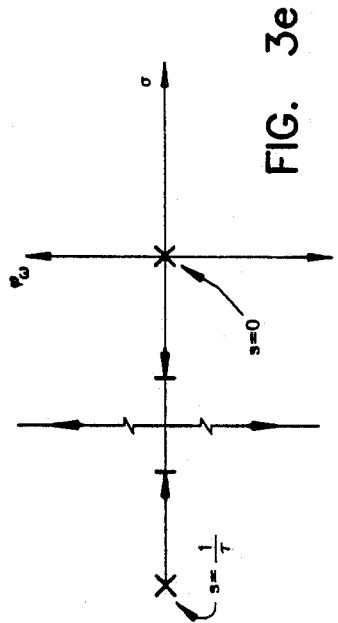
FIG. 3e
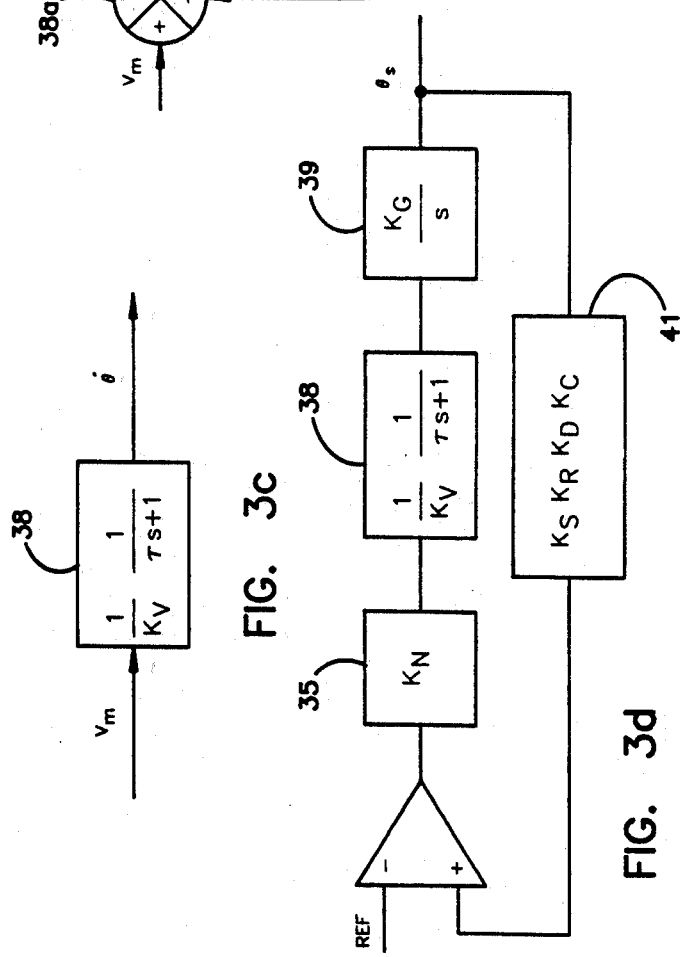
FIG. 3c
FIG. 3d

CONTROL LOOP FOR MOTORIZED SHUTTER OPERATION

BACKGROUND OF THE INVENTION

The present invention pertains to a control system for automatic adjustment of the amount of light supplied to a target from a light source, and more particularly to a control system of the type incorporating a motor for positioning a shutter. The invention is especially adapted for use with a video camera used in medical inspections.

Cameras using high intensity light sources are desirable because of their natural color output and find application in surgical inspection devices. One difficulty with cameras using high intensity light sources in surgical inspection is controlling the amount of light supplied from the light source and reflected from the target to the camera. The amount of light reflected from the target is a function of the target distance, that is the distance from light guides used with the video camera to the target, and the reflectance of the target. Controlling the amount of light reflected from the target is difficult as the target distance and the reflectance of the target change as the surgical inspection device moves through the body.

A known system for surgical inspection includes a high intensity light source and a shutter for controlling the amount of light supplied from the light source, which is applied to a first light guide in order to illuminate a target. A second light guide passes light from the target to a video camera, which senses the amount of light reflected from the target in order to adjust the shutter position. Although this system provides automatic control of the light supplied to the target according to the amount of light reflected from the target, the system has certain undesirable characteristics and features. The known system utilizes a shutter sensor to sense the amount of light passing through the shutter and another sensor to sense the light level of the signal output from the video camera. The shutter light sensor of this known system presents several difficulties. The shutter light sensor is expensive and difficult to obtain. Additionally, the known systems include six calibration potentiometers, and thus requires a significant amount of calibration time when the system is initially set up. Furthermore, the system must be recalibrated each time the light source is replaced. Because the lamps have a relatively short life expectancy (approximately 250 hours), a large amount of time is spent recalibrating the system. A further difficulty in using the prior art systems is that the sensors must be mechanically aligned as part of the calibration procedure.

An additional consideration in providing a motorized control for a shutter is the response time of the system. The response time of the known system is a function of the individual time constants of the sensors and the motor. As a result, the known system is slow in responding to changes in the target distance and reflectance, and thus the system is often supplying an improper amount of light to the target during dynamic situations.

SUMMARY OF THE INVENTION

The invention overcomes the difficulties of the prior art by providing a shutter control system including a motor and an electronic drive circuit, which does not use a shutter light sensor and has a lower time constant for the motor and drive circuit. According to one aspect of the invention, the electronic drive circuit is coupled to a video camera in order to detect the intensity of the light received by the video camera, and the drive circuit is responsive to the light intensity detected by the video camera and an output signal from the motor for adjusting the position of a shutter.

By placing the motor in a closed-loop control circuit, the motor response becomes a factor in system operation. If the gain of the system is increased to compensate for the closed loop control system operation, the system becomes unstable. According to another aspect of the invention, this difficulty is overcome by feeding a signal from the motor back to the drive circuit to drive the motor. This allows the system gain to be increased, since the time constant of the circuit is reduced, without causing oscillation, and makes the motor static friction, or stiction, appear to be less than it actually is. A system may thus be provided which does not include a light sensor for measuring the light passing through the shutter. Thus, the operation of the system is improved, and because the system does not require potentiometer adjustment, calibration requirements are significantly reduced.

According to another aspect of the invention, a shaft speed sensor is provided for sensing electrically the back EMF from the motor. Thus, the system does not require mechanical-elements for sensing the shaft speed. Such mechanical elements increase the cost of the overall system as well as increasing the load on the motor.

These and other objects, advantages and features of the invention will become apparent upon review of the following specification in combination with the drawings.

BRIEF DESCRIPTION OF THE DRAWINGS

FIGS. 3a, 3b and 3c are system control block diagrams of the motor per se;

FIG. 3d is a system diagram of the overall system;

FIG. 3e is a root locus plot diagram of the system illustrated in FIG. 3d;

DETAILED DESCRIPTION OF THE PREFERRED EMBODIMENTS

Figure 1:
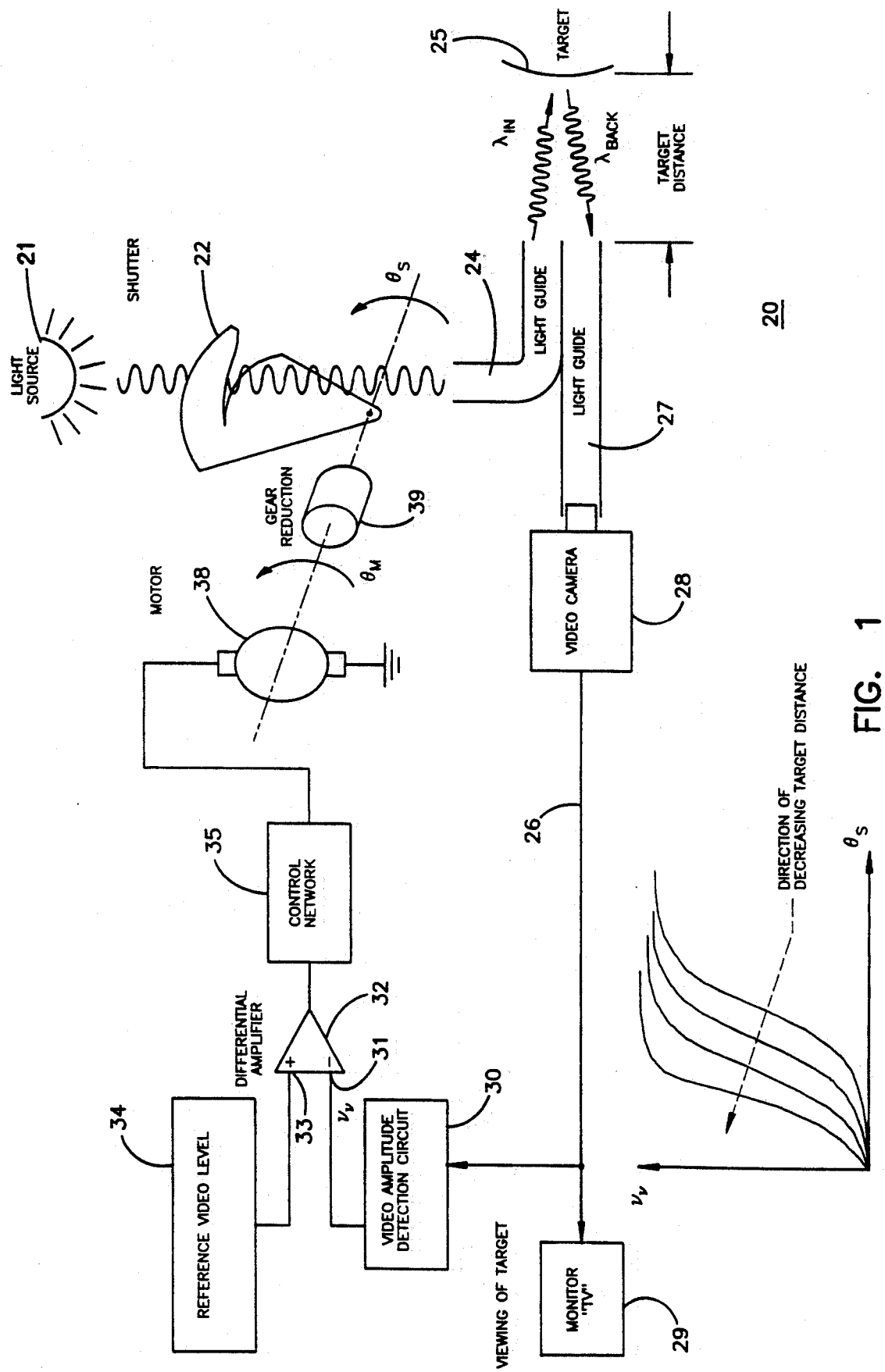
FIG. 1 illustrates a video system according to the invention.

Referring now specifically to the drawings, and the illustrated embodiments depicted therein, a video system 20 for a surgical inspection device includes an ultrabright light source 21, which is most preferably a metal halide lamp which may, for example, be powered by the power supply set forth in U.S. patent application Ser. No. 07/341,573, entitled POWER SOURCE FOR METAL HALIDE LAMPS AND THE LIKE, filed Apr. 21, 1989 by James C. Cook, II and Lawrence Eccleston. A shutter 22 controls the amount of light which leaves light source 21 and enters light guide 24. The light in light guide 24 is applied to a target 25. As the surgical inspection device moves, light guide 24, and an associated light guide 27, will be positioned in front of different targets each of which has a different reflectance, which is defined as the ratio of light intensity output from light guide 24 to light intensity input to light guide 27. The reflected light waves are supplied to a video camera 28 via light guide 27. Video camera 28 generates an output signal 26 from the light which passes through light guide 27. Output signal 26 is supplied to both a TV monitor 29 and a video detection circuit 30. An output $V_v$ from video detection circuit 30 is supplied to an inverting input 31 of a differential amplifier 32. The differential amplifier receives a reference potential, generated by a reference source 34, at a non-inverting input 33, and generates an output control signal to a motor control network 35. The motor control network 35 generates a drive signal $V_m$ which is applied to motor 38 which, in turn, adjusts shutter 22 thru a gear reduction system 39.

Figure 2:
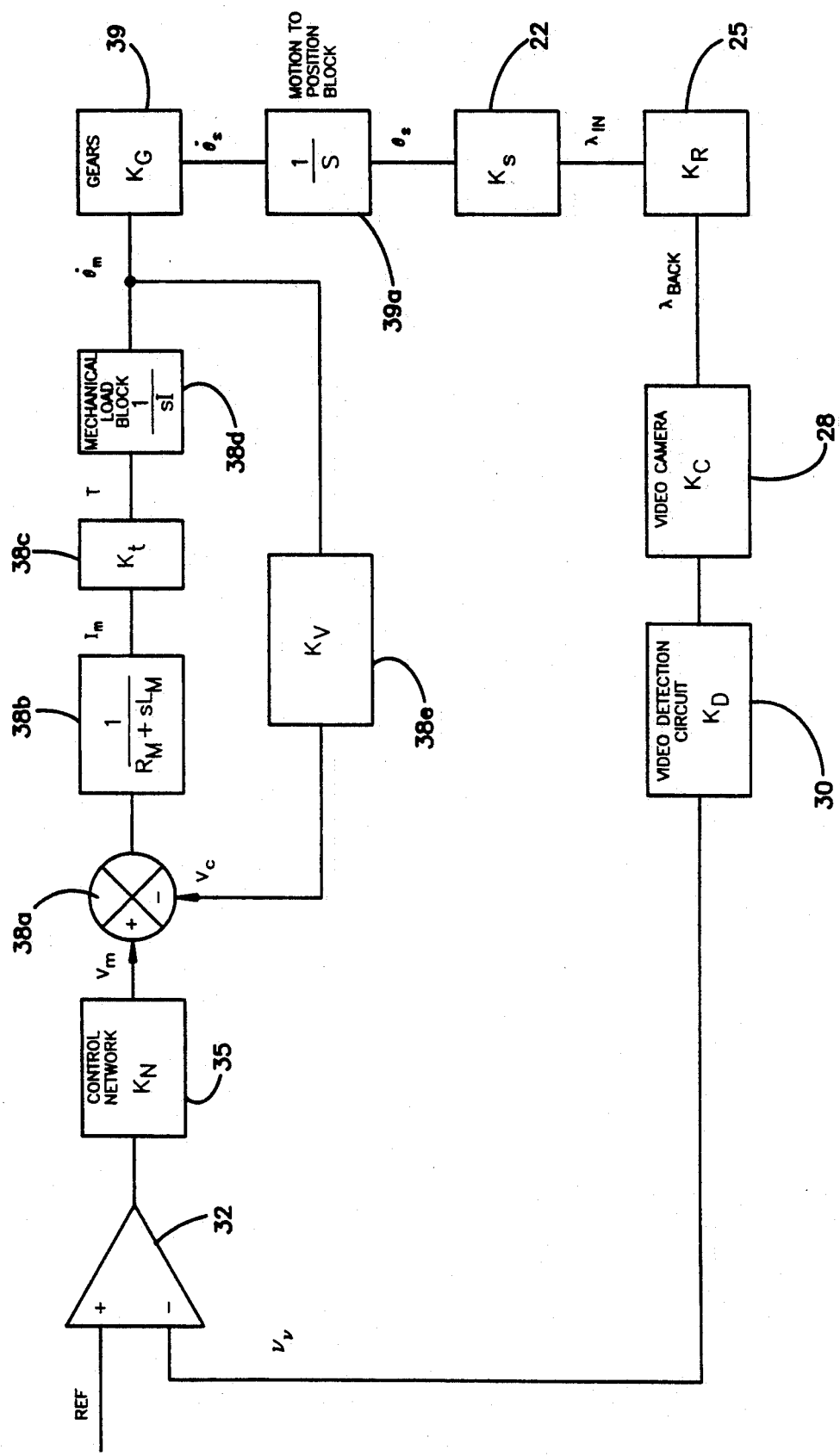
FIG. 2 is a system control block diagram of the system illustrated in FIG. 1.

The system of FIG. 1 includes a number of elements having respective control system transfer functions which contribute to the performance of the overall system (FIG. 2). Thus, target 25 has a reflectance represented by a reflective transfer characteristic $K_R$ which is the reflected light $\lambda_{BACK}$ as a function of the light $\lambda_{IN}$ supplied to the target. Video camera 28 has a transfer function $K_C$ which represents the output signal of the camera as a function of $\lambda_{BACK}$. The video detection circuit 30, in turn, has a transfer characteristic $K_D$ which represents the output signal $V_v$ as a function of the output signal from video camera 28. Control network 35 has a transfer function $K_N$, which in turn determines the value of the motor drive signal $V_m$. Motor 38 includes a shaft having a rotational shaft velocity $\dot{\theta}_m$ established as a function of signal $V_m$. The motor includes an impedance 38B defined by motor resistance component $R_M$ and motor inductance component $L_M$, a motor torque function 38C defined as a constant $K_t$, a motor inertia function 38D defined as a motor inertia component $I_M$, a gear inertia component $I_G$ and a reflected load inertia $I_L$. The motor further includes a counter EMF function 38E defined as a constant $K_V$. Counter EMF function produces a signal $V_c$ as a function of $\dot{\theta}_m$. Signal $V_c$ is supplied to a negative input of a summing junction 38A which receives motor drive signal $V_M$ as a positive input. Gear reduction system 39 has a transfer function $K_G$, converting rotational motor shaft velocity to rotational shutter velocity. Shutter position is an integral of shutter velocity and is represented by block 39A. The position of shutter 22 determines the amount of light from light source 21 which is supplied to light guide 24, and thus the shutter constant $K_S$ represents $\lambda_{IN}$ as a function of $\theta_s$.

Somewhat more particularly, the function of motor 38 may be represented by the system diagram illustrated in FIG. 3a. Because the L/R time constant of the motor is on the order of 10.4 microseconds, whereas the time response of the system of FIG. 1 is between 0.1 and 1.0 second, the inductance of the motor may be neglected. Control block 38B thus may be simplified to the transfer function $1/R_M$, which represents the effective motor impedance. Converting the system diagram of FIG. 3a into the time domain, control block 38D becomes $1/I \int \Box dt$. It may thus be seen that the time constant $\tau$ of motor 38 is equal to $(R_M I)/(K_T K_V)$. Using the time constant $\tau$, it can be seen that block 38 (FIG. 3c) represents the transfer characteristic of the motor, and thus $\dot{\theta}_m/V_m$ equals $1/(K_V(\tau s+1))$. Substituting block 38 into FIG. 2, and substituting block 41 for blocks 22, 25, 28 and 30, the system of FIG. 1 is represented by the system diagram of FIG. 3d. The system illustrated in FIG. 3d produces a root locus diagram having poles at $-1/\tau$ and 0 as illustrated in FIG. 3e.

The simple model of FIG. 3d is unconditionally stable for all gains, whereas the actual system constructed according to FIG. 2 may be unstable. In evaluating an actual system, it was found that there is an open loop pole at $S=-R_M/L_M$ on the negative real axis. There is also a pole in the video detection circuit 30 at around 30 Hz. Through experimentation, it was also found that a mechanical resonance occurs at between 15-20 Hz, which was discovered to be due to the spring effect of the plastic gears used in reduction gears 39 and represents two additional complex poles. It was thus found that at about 15-20 Hz, the shutter and motor shaft move approximately 180° out of phase simply due to the spring effect of the plastic. Additionally, other poles likely exist such that the above illustrated poles are most likely not the only additional poles.

It was discovered that the system represented by FIG. 2 oscillates continuously for high gains. When the system gain is reduced, oscillation only occurs when the target is close to the light guides. This is due to the amount of light which is reflected from the target to the camera when light guides 24 and 27 are positioned close to the target. By reducing the gain, the system becomes borderline stable, and any small increase in the gain causes oscillation. If the gain is lowered below marginal stability, the shaft will not move as a result of static friction, or stiction, and the system becomes stalled. Furthermore, when the target and the video camera are separated by large distances, the system will stall at those gain settings which are marginally stable for a short target distance.

Ideally, in operation, if there is a small difference between the reference signal and the feedback signal $V_V$, voltage $V_m$ will have a small magnitude and the signal applied to the motor will likewise have a small magnitude. No matter how small the feedback signal $V_v$ is, the motor should be responsive to that small voltage to cause the motor shaft to move to compensate for this difference. Ideally, the shaft velocity would be 0 if the difference signal is 0, and the system will always drive to 0 difference signal. Consequently, the shutter would be positioned exactly where it should be. Such a system would be a zero error system found in systems lacking friction, including such as the integrators 1/S block 38D in FIG. 2. Because viscous friction does not effect a zero error system, the system will still operate according to the ideal system when viscous friction is present.

Non-viscous motor static friction, or stiction, unlike viscous friction, effects a zero error system detrimentally. A system including non-viscous motor stiction is illustrated in block 43. Striction, as used in this application, is the stickiness or friction at rest and at all driving speeds of the motor. The non-viscous motor stiction $T_r$ is generally independent of the motor shaft speed $\dot{\theta}_m$. If the motor shaft is not moving, and the difference signal from difference amplifier 32 is not large enough to create a motor torque greater than the stiction, the motor shaft will not rotate. Furthermore, if the motor shaft is moving, but the motor torque is less than the motor stiction, the motor shaft will come to a halt. Thus, it can be seen that if gain is not high enough, the system will stall regardless of the difference signal magnitude output from difference amplifier 32. Further, even when the system gain is set to a stable level, when operating at one target distance, it may stall if the target distance is increased or the video reference signal is near saturation. Both of these effectively reduce the gain at the operating point of the motor.

Other characteristics of the system according to FIG. 2 detrimentally effect operation of the system. If the gain is set too high, the system will oscillate. Further, the non-viscous motor stiction introduces hysteresis into the system so that the system will not always drive to the ideal shaft position. For example, it was found that if the light guides move slowly to the same fixed position on the target from the right and the left, there will be a different light level reflected from the target.

It was discovered that the system diagram of FIG. 5 represents the actual operating conditions of the system according to FIG. 2. The motor static friction $T_r$, illustrated in logic block 43, includes not only components from the brushes and bearings, but also a potentiometer, not shown, which produces a shaft position signal for display purposes. Although this monitoring potentiometer forms no part of the control loop in the preferred embodiment, it contributes a major portion of the stiction. In fact, the stiction contributed by the monitor potentiometer exceeds that from the motor per se.

Figure 4:
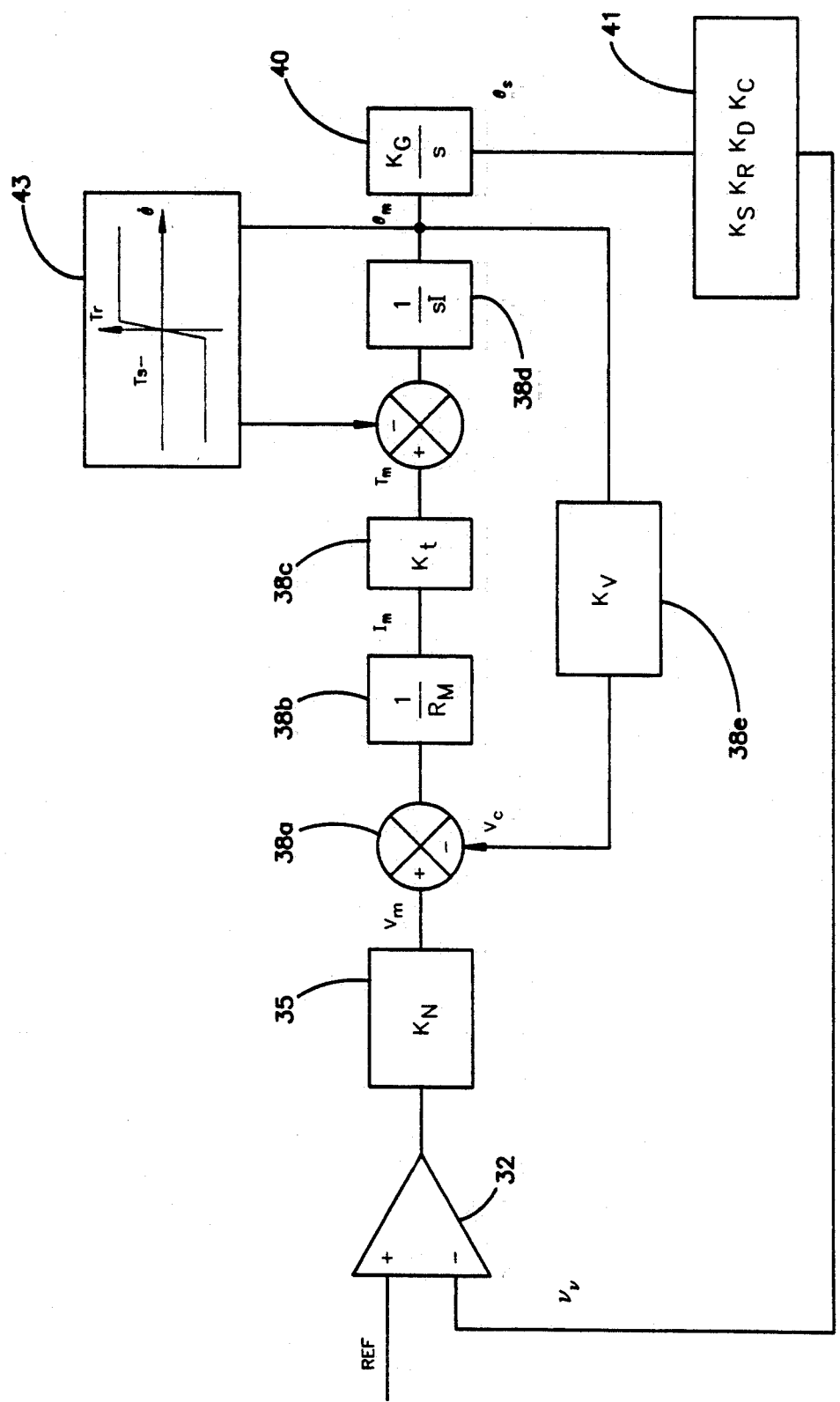
FIG. 4 is a system control block diagram of the system in FIG. 1 including a static friction feedback block.
Figure 5A:
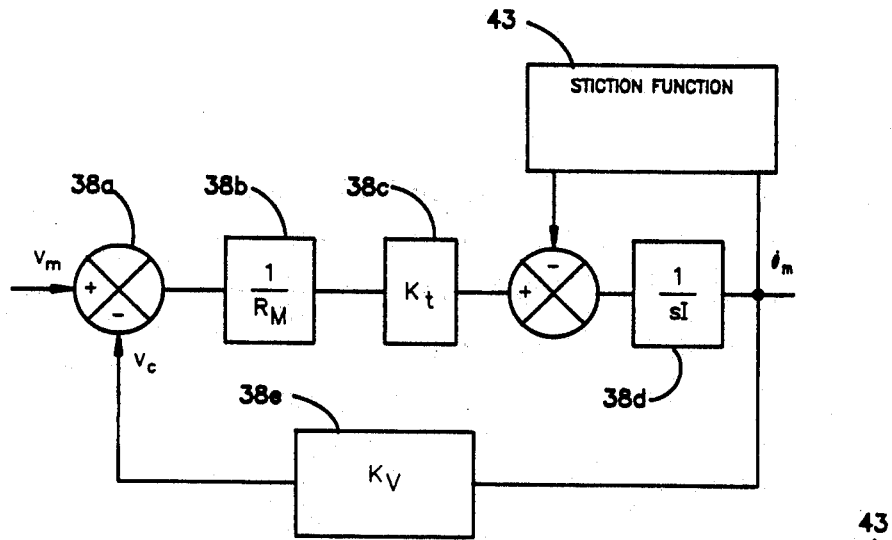
FIG. 5a is a system control block diagram of the motor per se, including the static friction block as illustrated in FIG. 4.
Figure 5B:
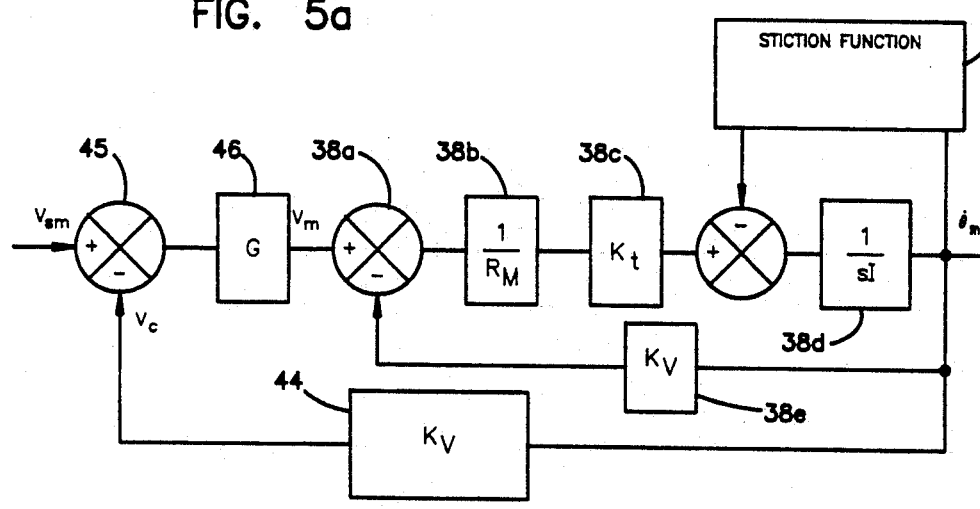
FIG. 5b is a system diagram of the motor illustrated in FIG. 5a including an additional feedback path.

FIG. 5a illustrates a motor transfer function for the system of FIG. 4 which includes a stiction function feedback component. To overcome the problem of stiction, or non-viscous motor friction described above, an additional feedback path 44 (FIG. 5b) is provided between the output $\dot{\theta}_m$ and the gain block 46. The transfer functions of FIG. 5b represent a motor which reduces the time constant of the system by a factor of 10, as well as provides a motor having a ten times higher frequency response, whereby the gain may be made significantly higher without causing oscillation. It was discovered that by neglecting the stiction function 44 of the motor in the control function, as illustrated in FIG. 5b, the gain of the new electronically equivalent motor $G_{SM}$ is described by the following equation:

$$G_{SM}(S) = \frac{\dot{\theta}_M}{V_{SM}} = \frac{1}{K_V} \frac{G}{1+G} \frac{1}{\frac{\tau}{G+1}S + 1}$$

Additionally, for a large gain G, G+1 approaches G such that the motor gain may be represented by the following equation:

$$G_{SM}(S) \approx \frac{1}{K_V} \frac{1}{\frac{\tau}{G}S + 1}$$

Thus, the motor represented by FIG. 5b operates G times faster than the motor of FIG. 2. If G is set approximately equal to 10, the motor will operate with a time constant approximately 10 times faster than without the additional feedback path.

The system of FIG. 5b is realized using an electronic switch 48 (FIG. 5c) having an output connected to a summing junction 38A and an input which is selectively connected to either B, the output of gain block 46, or to A, which is connected to signal ground potential. Additionally, the motor impedance block 38B is connected via a sample and hold circuit 49 and an equivalent motor impedance block 50 to a summing amplifier 45. By providing a connection from the output of gain block 46 to summing junction 38A, which is connected, by way of example 99.9% of the time, the average voltage over each cycle of the motor is, for all practical purposes, the same as though block 46 is directly connected to combiner 38A. The practical effect is that the gain of block G is changed from G to GD, where D is the fractional duty cycle which the wiper of switch 48 is connected to node B. Most preferably, the frequency of the switch cycle is much higher than the frequency response of the system. During those times when the wiper arm of switch 48 is connected to node A (ground potential), no voltage is supplied to motor 38 and the current from the counter EMF of the motor is measured. The measured current is directly proportional to the shaft speed of the motor. Most preferably, 0 volts is applied to the motor long enough for the current stored by the inductive impedance of the motor to reach a fixed value. The counter EMF signal from the motor is sampled while 0 volts is applied to the motor, and held by the sample and hold circuit 49 until zero volts is again applied to the motor. The circuit of 6c thus effectively simulates the circuit FIG. 5b. Furthermore, because the shaft speed is measured electrically, a mechanical shaft speed sensor is not required.

Figure 5C:
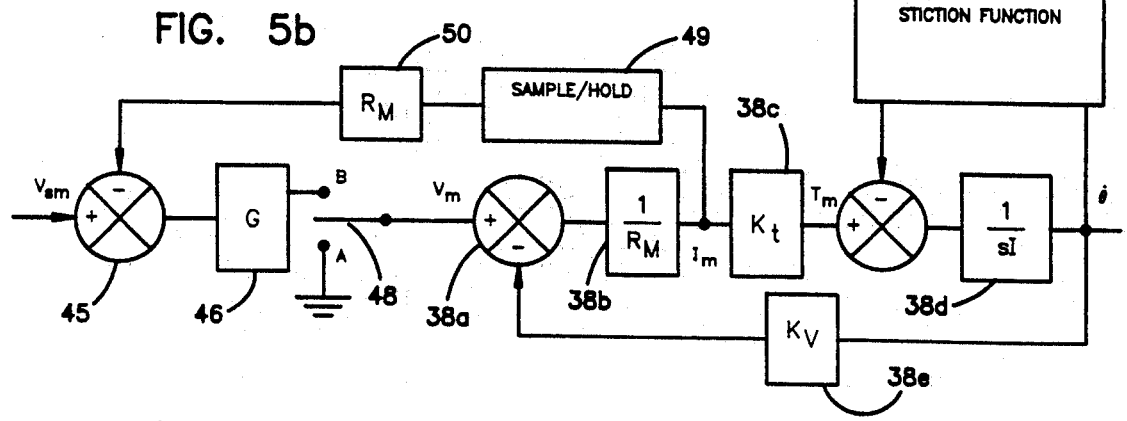
FIG. 5c is a system diagram of the motor including a sample and hold feedback system for simulating the system of FIG. 5b.
Figure 6:
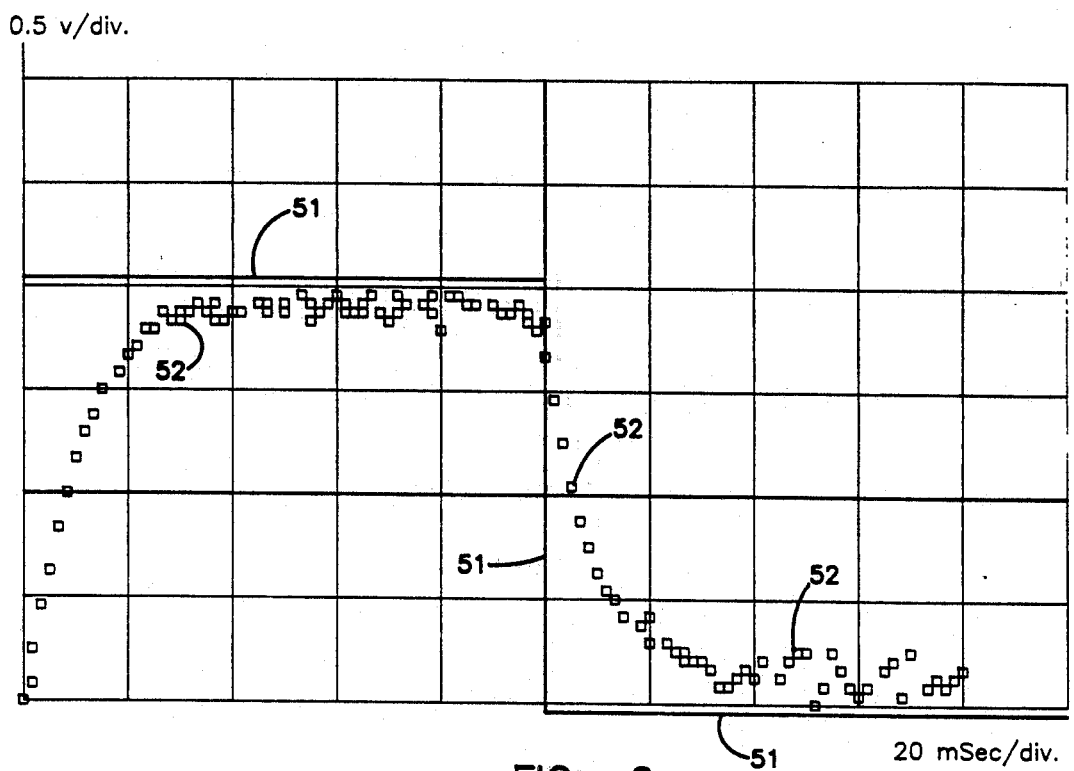
FIG. 6 illustrates the response of the system of FIG. 5c to a step input.

FIG. 6 illustrates the sampled current step response to a step input 51 applied to an equivalent motor circuit having the transfer function of FIG. 5c. The step input 51 is applied as the $V_{SM}$ input signal to summing amplifier 45. As can be seen from the sampled output signal 52 from the system, the shaft of motor 38 closely follows the square wave input $V_{sm}$ and responds quickly to the input signal.

Figure 7:
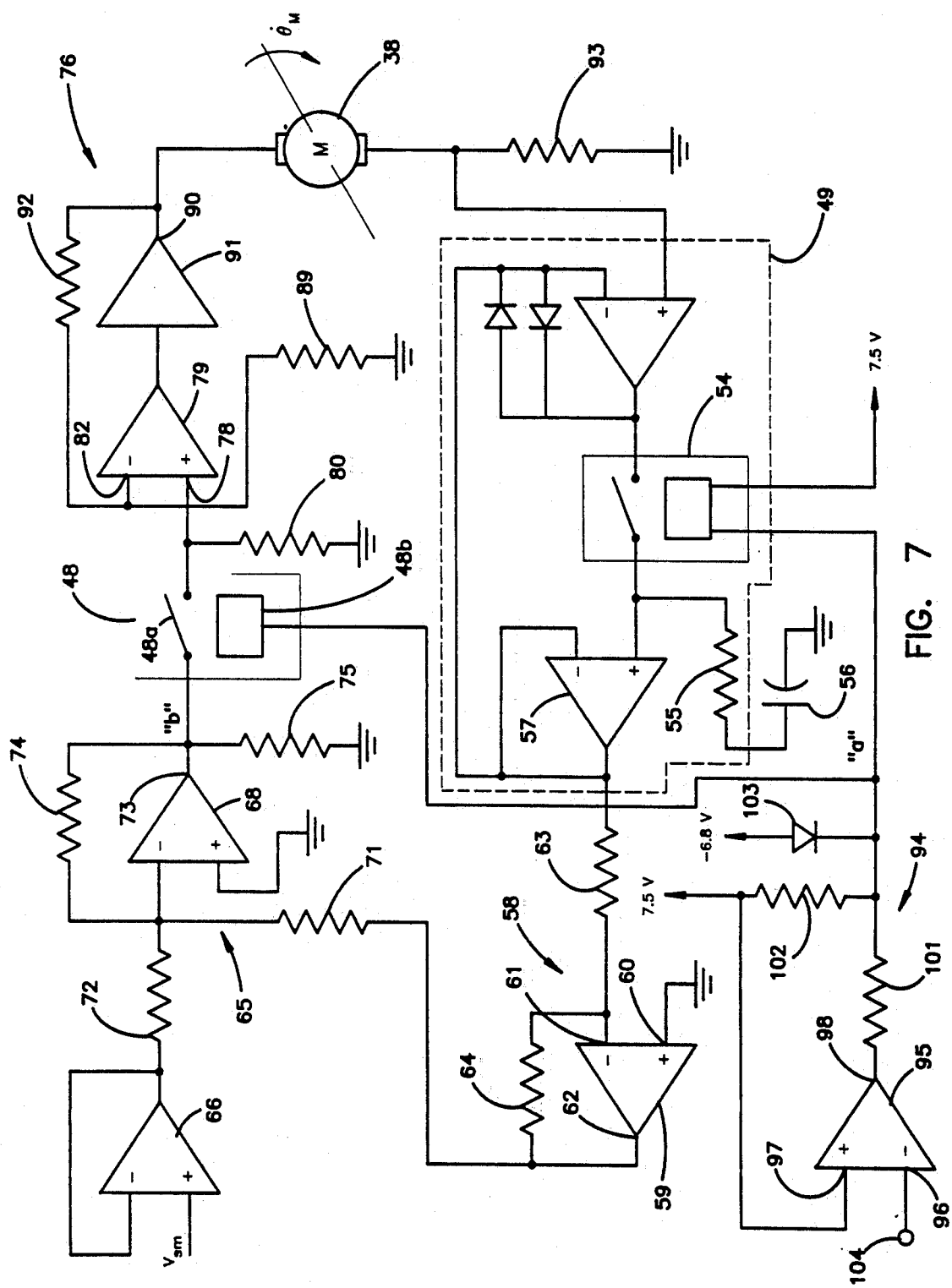
FIG. 7 is a block diagram illustrating a motor and drive elements of the system in FIG. 5c.

A schematic diagram of a motor system according to FIG. 5c is illustrated in FIG. 7. Sample and hold circuit 49 may be provided as an integrated circuit, such as IC No. SNC298 manufactured by Burr-Brown. Circuit 49 includes a buffer amplifier 53, a switch 54, an amplifier 57 and a resistor 55 for connection in series with an external capacitor 56 which holds the charge sampled by switch 54. The output of buffer amplifier 53 presents a low impedance to hold capacitor 56 and the input of amplifier 57 presents a high impedance when switch 54 is open, whereby the capacitor 56 will charge quickly when switch 54 is closed and hold the sampled potential for the period when switch 54 is open.

An inverter 58 is coupled to the output of sample and hold circuit 49. The inverter includes an operational amplifier 59, which may, for example, be provided by an IC No. LM660C operational amplifier. The non-inverting input 60 of amplifier 59 is connected to ground potential. The inverting input 61 is connected via resistor 63 to the output of amplifier 57. Output 62 of amplifier 59 is connected via resistor 64 to inverting input 61 of the amplifier 59. Preferably, resistors 63 and 64 have the same impedance whereby the inverter 58 provides unity gain and simply inverts the output of sample-and-hold circuit 49.

Summer and gain circuit 65 combines the signal output from comparator 32 (FIG. 1) and provides gain G. The summing amplifier and gain circuit includes a voltage follower amplifier 66 which acts as a buffer and passes signal $V_{SM}$ that is outputted by differential amplifier 32. Summing amplifier and gain circuit 65 further includes a summing amplifier 68, which may be implemented by an IC No. LM660C operational amplifier. The non-inverting input 69 of amplifier 68 is connected to ground potential. The inverting input 70 is connected via a resistor 71 to output 62 of amplifier 59, and via a resistor 72 to the output of voltage follower 66. The output 73 of amplifier 68 is connected via resistor 74 to inverting input 70 of amplifier 68. Amplifier 68 thus adds the signals from voltage follower 66 and inverter 58 and outputs the sum of these signals at output 73. The resistors 71, 72 and 74 are selected such that amplifier 68 provides gain G for the equivalent motor circuit. Resistor 71 may, for example, be a 3.3 Kohm resistor, resistor 72 may be a 5.1 Kohm resistor, and resistor 74 may be a 43 Kohm resistor. A resistor 75 is connected between output 73 and ground.

Switch 48 includes a bilateral element 48A which selectively connects the output 73 of amplifier 68 to a non-inverting input 78 of an amplifier 79, under the control of control elements 48B. Switch 48 may be provided by an IC No. CD 4066B bilateral switch, with output 73 of amplifier 68 connected to one input/output of the bilateral switch 48 and input 78 connected to the other input/output of the bilateral switch. Input 78 is also connected via a resistor 80 to ground potential. The output of amplifier 79 is connected to the input of a buffer amplifier 91. The inverting input 82 of amplifier 79 is connected to ground potential via a resistor 89 and is connected to an output 90 of buffer amplifier 91 via a resistor 92. Amplifier 79 may be implemented by an IC No. LM2904 operational amplifier. Amplifier 91 may be implemented by an IC No. LH0002 current amplifier. Output 90 of buffer amplifier 91 is connected to the positive terminal of motor 38 and applies output control signals for controlling the rotational position of the motor shaft. A resistor 93 is connected between the negative terminal of motor 38 and ground potential. The junction of the motor and resistor 93 is connected to the non-inverting input of amplifier 53.

Control signals are generated for switches 48 and 54 by pulse generating circuit 94. Pulse generating circuit 94 includes a comparator 95, which may be implemented by an IC No. LM2903, low offset voltage comparator. Comparator 95 has an inverting input 96 connected to receive a pulse train from an input 104. An output 98 of amplifier 95 is connected via a resistor 101 and a resistor 102 to supply voltage $V_2$ (7.5V) which is also provided to a non-inverting input 97 of amplifier 95. The cathode of a diode 103 is connected to the junction of resistors 101 and 102 and the anode of diode 103 is connected to a negative voltage $V_3$. Diode 103 prevents the output voltage from pulse generator 56 from going below a negative voltage $V_4$. Thus, the pulse generator will generate a signal which switches between voltage $V_2$ and voltage $V_4$ for driving switches 48 and 49. For example, voltage $V_2$ may be 7.5 volts, voltage $V_3$ may be $-6.8$ volts, and voltage $V_4$ may be $-7.5$ volts.

In operation, signal $V_{SM}$ from differential amplifier 32 is combined with the signal output from inverter 58 and amplified by amplifier 68. When switch 48A is closed, the output signal from amplifier 68 will be applied to drive network 76 which outputs a drive current to motor 38. When switch 48A is open, switch 47 will close charging capacitor 56. The potential on capacitor 56 is held while switch 49 is open, whereby the potential is inverted by amplifier 59 and the inverted signal is combined, with signal $V_{SM}$ to control the motor.

Figure 8A:
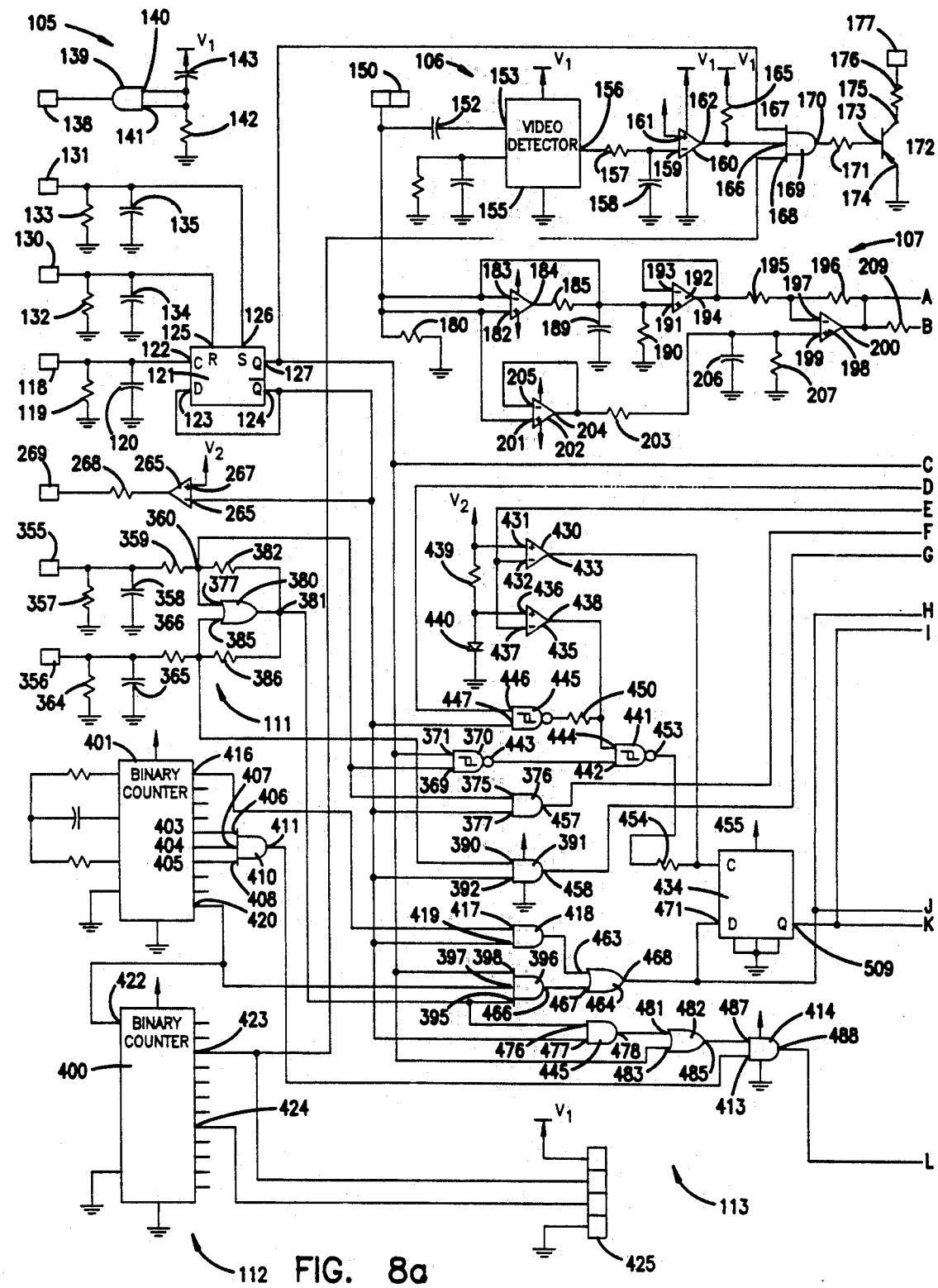
FIGS. 8a, 8b, and 8c are schematic diagrams of the system in FIG. 7.
Figure 8B:
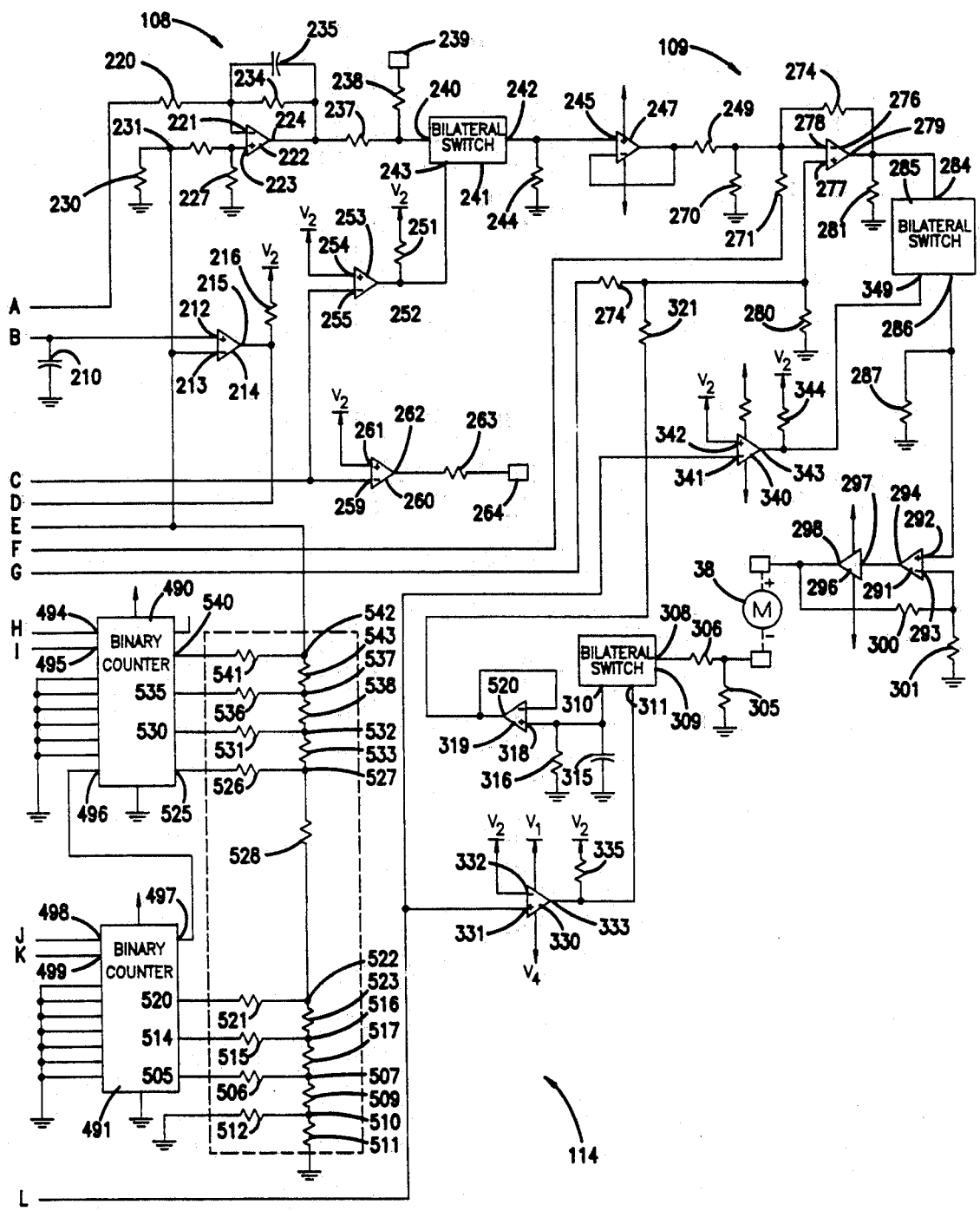
Figure 8C:
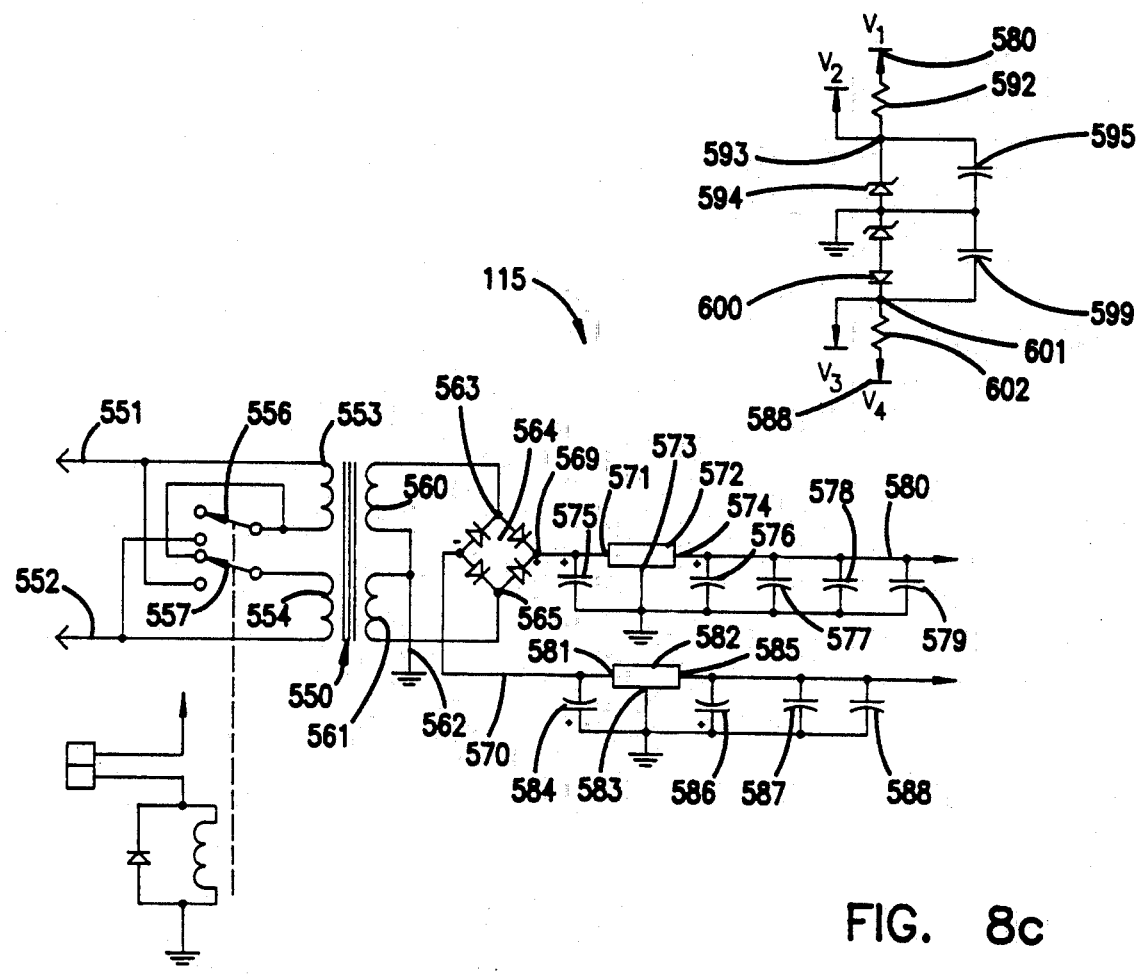

The schematic diagram of the circuit according to FIG. 1 includes a mode select portion 105 (FIG. 8a), a video indicator portion 106, a video detector portion 107, a differential amplifier portion 108 (FIG. 8b), a motor position control portion 109, an up/down input portion 111 (FIG. 8a), a timing signal portion 112, a logic control portion 113, a reference set portion 114 (FIG. 8b), and an AC/DC power supply portion 115 (FIG. 8c). The schematic diagram is described below with reference to FIGS. 8a–8c. The mode select portion 105 includes manual/automatic mode select input 118 for selecting manual or automatic shutter control. The mode select input 118 is connected to receive a mode select signal from a switch (not shown) which may, for example, be a bounce switch which provides a high level logic signal to input 118 whenever the bounce switch is pressed. The mode select signal is supplied via a resistor 119 and a capacitor 120 to a clock input 122 of a data flip-flop 121. Flip-flop 121 may be implemented by an IC No. CD4013B data flip-flop. Capacitor 120 is connected between input 118 and ground to remove high frequency noise resulting from actuation of the mode select button connected to input 118. A data input 123 is connected to an inverted output 124, which corresponds to the output of flip-flop 121. When a reset input 125 and a set input 126 of flip-flop 121 have a zero logic level applied thereto, actuation of the mode select button connected to input 118 will cause a non-inverted logic output 127, which corresponds to the Q output of flip-flop 121, to change state. Output 127 will change state because data input 123 is connected to follow the inverted output 124 of flip-flop 121 upon each clock transition.

Reset input 125 is connected to wake-up mode select input 130 via a parallel connection of a resistor 132 and a capacitor 134 which are connected between input 130 and ground. Set input 126 is connected to a wake-up mode select input 131 via a parallel connection of a resistor 133 and a capacitor 135, resistors 133 and 135 connected between input 131 and ground. Capacitors 134 and 135 filter out high frequency noise which is generated when inputs 130 or 131 are connected to output 138. Resistors 132 and 133 provide a discharge path for capacitors 134 and 135. Output 138 has a high logic level thereon which is generated by ANDGATE 139. A high logic level is applied to both inputs 140 and 141 of ANDGATE 139 which are connected to a junction of a capacitor 143 and a resistor 142 connected in series between supply voltage $V_1$ and ground potential. Thus, ANDGATE 139 outputs a high logic level to output 138 which is applied to one of inputs 130 and 131 to select either manual or automatic motor control mode when the system is powered up.

Video indicator portion 106 is connected to video input 150 to receive an input signal from video camera 28 (FIG.1). Capacitor 152 is connected between input 150 and an input 153 of a video signal detector 155. Video signal detector 155 may be implemented by an LM1883 integrated circuit manufactured by National Semiconductor. Output 156 of integrated circuit 155 is connected to one end of a resistor 157, the other end of resistor 157 connected via capacitor 158 to ground. The junction of resistor 157 and capacitor 158 is connected to inverting input 159 of comparator 160. Comparator 160 may be implemented by an LM2901 comparator. A non-inverting input 161 of amplifier 160 is connected to voltage $V_2$. Output 162 of amplifier 160 is connected to pull-up resistor 165 and input 166 of ANDGATE 169. ANDGATE 169 may be implemented by a CD4073B ANDGATE. Input of ANDGATE 169 is connected to receive timing signals from timing portion. Input of ANDGATE 169 is connected to output 127 of flip-flop 121. An output 170 of ANDGATE 169 is connected via a resistor 171 to gate 173 of NPN transistor 172. NPN transistor 172 may, for example, be implemented by a PN2222 transistor. The collector 175 of transistor 172 is connected via a resistor 176 to status indicator output 177. An emitter 174 of transistor 172 is connected to ground potential.

Video detector portion 107 includes a resistor 180 connected between video input 150 and ground potential. Input 150 is connected to a non-inverting input 182 of a comparator 181. Comparator 181 may be implemented by an IC No. 2903 comparator. Output 184 of comparator 181 is connected to one end of a resistor 185, the other end of resistor 185 is connected to the inverting input 183 of comparator 181 and the positive terminal of capacitor 189. Resistor 185 is necessary because the output transistor in comparator 181 cannot go from on to off instantaneously. Thus, resistor 185 is provided to prevent capacitor 189 from being pulled too far negative before the internal transistor is fully off. A negative terminal of capacitor 189 is connected to ground. A resistor 190 is connected in parallel with capacitor 189 such that one end of resistor 190 is connected to a non-inverting input 191 of an amplifier 194, and the other terminal of resistor 190 is connected to ground. Resistor 190 provides a discharge (decay) path for capacitor 189 when the negative peak level rises toward zero. Amplifier 194 may be implemented by an LF347 wide band width operational amplifier.

An output 194 of amplifier 192 is connected to the inverting input 193 of amplifier 192 and is thus connected as a voltage follower. A resistor 195 is connected between output 194 and inverting input 197 of amplifier 198. Amplifier 198 may be implemented by an IC No. LF347 operational amplifier. A resistor 196 is connected between output 200 and inverting input 197 of amplifier 198. Non-inverting input 199 of amplifier 198 is connected via a resistor 203 to an output 204 of an amplifier 202. Amplifier 202 has a non-inverting input 201 connected to video input 150 and an output connected to an inverting input 205 whereby amplifier 202 operates as a voltage follower. A capacitor 206 and a resistor 207 are connected in parallel between non-inverting input 199 of amplifier 198 and ground potential, and thus provide a filter for signals output from buffer amplifier 202. One end of a resistor 209 is connected to output 200 of amplifier 198, and the other end of resistor 209 is connected via capacitor 210 to ground potential. Resistor 209 and capacitor 210 are thus connected as a low pass filter and provide an integrator for the signal output by amplifier 198. A junction of resistor 209 and capacitor 210 is connected to a non-inverting input 212 of comparator 214. Comparator 214 may be implemented by an LM 2901 comparator. An inverting input 213 of comparator 214 is connected to reference portion 114. Output 215 of comparator 214 is connected to a pull-up resistor 216. Pull-up resistor 216 is connected to supply voltage $V_1$.

Difference amplifier portion 108 includes a resistor 220 connected between a non-inverting input 221 of an amplifier 222 and output 200 of amplifier 198. Amplifier 222 may be implemented by a LMC660C amplifier. A resistor 228 is connected between a junction 231 and non-inverting input 223 of amplifier 222. The non-inverting input 223 of amplifier 222 is connected to ground potential via a resistor 227. Junction 231 is connected to ground potential via a resistor 230. Junction 231 is also connected to reference potential portion 114. Output 224 of amplifier 222 is connected by the parallel connection of a resistor 234 and a capacitor 235 to the inverting input 221 of amplifier 222. Capacitor 235 prevents the LMC660C amplifier from going into saturation from high frequency changes and has a faster frequency response than system 20, and accordingly does not detrimentally effect system operation. Resistor 234 provides a gain and may, for example, provide a gain of 10. Output 224 is also connected by a resistor 237 to an input/output 240 of a bilateral gate 241. Bilateral gate 241 may be implemented by a CD4066B bilateral switch.

Input/output 240 is connected via a resistor 238 to a terminal 239. Terminal 239 is connected to a plurality of selectively switched resistors (not shown) which allow the system operator adjust the gain of the system. The system is adjusted using the switched resistors for video cameras which output video signals having different light intensities. Input/output 242 is connected via a resistor 244 to ground potential. Input/output 242 is also connected to a non-inverting input 245 of a voltage follower 247. Voltage follower 247 may be implemented by an LMC660C amplifier. Output 248 of voltage follower 247 is connected via a resistor 249 to motor control portion 109. Control input of 243 of bilateral switch 241 is connected via a pull-up resistor 251 to potential $V_2$. Input 243 is also connected to output 252 of comparator 253. Comparator 253 may be implemented by an LP365 comparator. Inverting input 254 of comparator 253 is connected to supply voltage $V_2$. Non-inverting input 255 of comparator 253 is connected to output 127 of data flip-flop 121.

System 20 includes two indicator outputs which indicate the control mode selected. A comparator 260 has an inverting input 259 connected to output 127 of flip-flop 121. Comparator 260 may be implemented by an LM2903 comparator. A non-inverting input 261 of comparator 260 is connected to supply voltage potential $V_2$. Output 262 of comparator 260 is connected via a resistor 263 to auto status lamp terminal 264. Accordingly, comparator 260 will provide a high level output signal to auto status lamp 264 whenever the input voltage applied to 259 is less than the supply voltage $V_2$. A comparator input 266 of a comparator 265 is connected to output 124 of flip-flop 121. A non-inverting input 267 of comparator 266 is connected to supply potential $V_2$. A resistor 268 is connected between an output of amplifier 265 and manual status lamp terminal 269. Comparator 265 may be implemented by an IC No. LP365.

Motor control portion 109 includes a resistor 270 connected between a resistor 249 and ground potential. Motor control portion 109 further includes a resistor 271 connected between junction 272 and logic control portion 113. A junction 273 of motor control portion 190 is connected by a resistor 274 to logic control portion 113. An operational amplifier 278 includes an inverting input 273 connected to junction 272 and a non-inverting input 277 connected to junction 273. Amplifier 278 may be implemented by an IC No. LMC660C amplifier. Output 279 of amplifier 278 is connected via a resistor 274 to junction 272. A non-inverting input 277 of amplifier 278 is connected via a resistor 280 to ground. Output 279 of amplifier 278 is also connected via a resistor 281 to ground. Output 279 of amplifier 278 is also connected to an input/output 284 of a bilateral switch 285. Bilateral switch 285 may be implemented by an IC No. CD4066B bilateral switch. Input/output 286 of bilateral switch 285 is connected via a resistor 287 to ground. Input/output 286 of bilateral switch 285 is connected to non-inverting input 292 of an amplifier 291. Amplifier 291 may be implemented by an IC No. LF347 amplifier. Output 294 of amplifier 291 is connected to input 297 of amplifier 296. Output 298 of amplifier 296 is connected via a resistor 300 to inverting input 293 of amplifier 291. Inverting input 293 of amplifier 291 is connected to ground potential via a resistor 301. Output 298 of amplifier 296 is connected to the positive terminal of motor 38. Motor 38 may be implemented by a 1516E012ST 15/1 485-1 manufactured by Micro Mo Electronics Inc, which includes gears 37.

Motor control portion 109 includes a sensor circuit connected to the negative terminal of motor 38 which provides an signal dependent upon the velocity of the motor shaft in motor 38. The sensor circuit is connected to one terminal of a resistor 305, the other terminal of resistor 305 connected to ground. The negative terminal of motor 38 is also connected via a resistor 306 to an input/output 308 of a bilateral switch 309. Bilateral switch 309 may be implemented by a CD4066B bilateral switch. An input/output 310 of bilateral switch 309 is connected to a non-inverting input 318 of an amplifier 319. Amplifier 319 may be implemented by an IC No. LMC660C amplifier. Input/output 310 of bilateral switch 309 is also connected to ground potential by the parallel connection of a capacitor 315 and a resistor 316. Amplifier 319 is connected as a voltage follower, the output 320 thereof connected via resistor 321 to non-inverting input 277 of amplifier 278.

Motor control portion 109 further includes circuit elements for generating timing signals for switches 285 and 309. An amplifier 330 has a non-inverting input 331 connected to receive timing signals from timing portion 112. Amplifier 330 may be implemented by an IC No. LP365 amplifier. An inverting input 332 of amplifier 330 is connected to supply voltage $V_2$. An output 333 of amplifier 330 is connected via a pull-up resistor 335 to voltage potential $V_2$. An output 333 is also connected to the control input 311 of a bilateral switch 309. An amplifier 340 has an inverting input 341 connected to a non-inverting input 331 of amplifier 330 whereby amplifier 341 receives the same timing signals as amplifier 330. Amplifier 340 may be implemented by an IC No. LP365 amplifier. Amplifier 340 includes a non-inverting input 342 connected to supply voltage $V_2$. Output 343 of amplifier 340 is connected via a pull-up resistor 345 to voltage potential $V_2$. Output 343 is also connected to control input 349 of bilateral switch 295.

Up/down input portion 111 includes an up input 355 and a down input 356. Up input 355 is connected via a capacitor 357 and a resistor 358 to ground potential. An input 355 is also connected through a resistor 359 to a junction 360. Down input 356 is connected via a capacitor 364 and a resistor 365 to ground potential. Capacitors 357 and 354 filter current spikes which occur when a switch (not shown) connected to inputs 355 and 356 closes to input a high logic level thereto. Resistors 358 and 365 provide a discharge path for the potential on capacitors 357 and 364 respectively. Input 356 is also connected via a resistor 366 to a junction 367. Junction 360 is connected to an input 369 of a Schmitt trigger NANDGATE 370, and to an input 375 of an AND-GATE 376. An input 371 of NANDGATE 370 is connected to output 127 of data flip-flop 121. An input 377 of ANDGATE 376 is connected to output 124 of data flip-flop 121. Junction 360 is connected to an input 379 of ORGATE 380. An output 381 of ORGATE 380 is connected via resistor 382 to junction 360. Junction 367 is connected to input 390 of ANDGATE 391. Input 392 of ANDGATE 391 is connected to output 124 of flip-flop 121. Junction 367 is connected to input 385 of OR-GATE 380. Output 381 of ORGATE 380 is connected via a resistor 386 to junction 367. Output 381 of OR-GATE 380 is also connected to input 395 of AND-GATE 396. Input 397 of ANDGATE 396 is connected to receive timing signals from timing portion 112. Input 398 of ANDGATE 396 is connected to output 127 of flip-flop 121.

Timing signal portion 112 comprises a 14-stage ripple carry binary counter 400 and a 12-stage ripple carry binary counter 401. Counter 400 may be implemented by an IC No. CD6060B binary counter having an internal clock. Three timing outputs 403, 404 and 405, which are the Q8, Q9 and Q10 outputs of 12-stage binary counter 401, are supplied to inputs 406, 407 and 408 of an ANDGATE 410. ANDGATE 410 generates a high logic level on an output 411 which is supplied to an input 413 of an ANDGATE 414 when outputs 403 to 405 simultaneously output a high logic level. An output 416, which is the Q4 output of binary counter 401, is connected to an input 417 of an ANDGATE 418 in logic control portion 113. An output 420, which is the Q14 output of binary counter 401, is connected to a clock input 422 of binary counter 400, as well as to input 397 of an ANDGATE 396. Output 423 of binary counter 400, which is the Q3 output, is connected to input 167 of ANDGATE 169. Output 424 of binary counter 400, which is the Q8 output, is connected to a 250 hour timer module output 425, as is output 423 of binary counter 400.

Logic portion 113 includes a comparator 430 having an inverting input 432 connected to reference portion 114, and a non-inverting input 431 connected to reference potential $V_2$. Output 433 of amplifier 430 is connected to a data input of a data flip-flop 434. Data flip-flop 434 may be implemented by an IC No. CD4013B. A comparator 435 comprises a non-inverting input 436 connected to reference generator 114, and an inverting input 437 connected to the junction of a resistor 439 and a resistor 440, which are connected in series between voltage potential $V_2$ and ground. Comparators 430 and 435 may be implemented by an IC No. LM2901 comparator. An output 438 of comparator 435 is connected to input 440 of Schmitt trigger NANDGATE 441. A Schmitt trigger NANDGATE 445 has an input 446 connected to output 215 of comparator 214. NAND- GATES 370, 441 and 445 may be implemented by an IC No. CD4093. An input 447 of NANDGATE 445 is connected to output 124 of flip-flop 121. An output 448 of NANDGATE 445 is connected via a resistor 449 to an input 440 of NANDGATE 441. Input 442 of NANDGATE 441 is connected to output 443 of NANDGATE 370. An output 453 of NANDGATE 441 is connected via a resistor 454 to data input 455 of data flip-flop 434. An output 457 of ANDGATE 376 is connected to resistor 271 to junction 272. An output 458 of ANDGATE 391 is connected via resistor 274 to junction 273. An input 460 of ANDGATE 418 is connected to output 124 of flip-flop 121. An output 461 of ANDGATE 418 is connected to input 463 of ORGATE 464. An output 466 of ANDGATE 396 is connected to an input 467 of ORGATE 464. An output 468 of ORGATE 464 is connected to clock input 471 of data flip-flop 434, as well as to the reference portion 114. An ANDGATE 475 has an input 476 connected to output 381 of ORGATE 380 and an input 477 connected to output 127 of data flip-flop 121. An output 478 of ANDGATE 475 is connected to an input 481 of an ORGATE 482. An input 483 of ORGATE 482 is connected to output 127 of data flip-flop 121. An output 485 of ORGATE 482 is connected to an input 487 of ANDGATE 414. An output 488 of ANDGATE 414 is connected to provide timing signals to the non-inverting input 331 of comparator 330 and the inverting input 341 of comparator 340. ANDGATES 376, 391, 418, 475 and 414 may be implemented by an IC No. CD4081B. ORGATES 380 and 482 may be implemented by an IC No. CD 4071B. ANDGATE 396 may be implemented by an IC No. CD4073B.

Reference portion 114 includes an up/down counter 490 and an up/down counter 491. Up/down counters 490 and 491 may be implemented by an IC No. CD4516 up/down counter. Up/down counter 490 comprises a clock input 494 which is connected to output 468 of ORGATE 464 and an input 495 connected to output 500 of data flip-flop 434. Binary counter 490 further includes an input 496 which is connected to output 497 of binary counter 491. Binary counter 491 further includes a clock input 498 connected to output 468 of ORGATE 464 and an input 499 connected to output 500 of data flip-flop 434. Thus, it can be seen that binary counters 491 and 490 are connected in series.

An output 505, which corresponds to the Q2 output of binary counter 491, is connected via resistor 506 to a junction 507. Junction 507 is connected via resistor 509 to junction 510. Junction 510 is in turn connected to ground potential via a parallel connection of resistors 511 and 512. An output 514, which corresponds to the Q3 output of binary counter 491, is connected by resistor 515 to a junction 516. Junction 516 is connected to junction 507 by a resistor 517. An output 520, which corresponds to output Q4 of binary counter 491 is connected through a resistor 521 to junction 522. Junction 522 is in turn connected to junction 516 by a resistor 523. An output 525, which corresponds to output Q1 of binary counter 490, is connected by resistor 526 to a junction 527, which in turn, is connected to junction 522 by resistor 528. An output 530, which corresponds to the Q2 output of binary counter 490, is connected by a resistor 531 to junction 532. Junction 532 is in turn connected by a resistor 533 to junction 537. An output 535, which corresponds to the Q3 output of binary counter 490, is connected by a resistor 536 to a junction 537 which in turn is connected by a resistor 538 to junction 532. Finally, an output 540, which corresponds to the Q4 output of binary counter 490, is connected by a resistor 541 to a junction 542. Junction 542 is in turn connected to a junction 537 by a resistor 543. Junction 542 is connected to inputs 432 and 437 of comparators 430 and 435, respectively, as well as being connected to junction 231 of comparator portion 108 and input 213 of comparator 214.

Power supply portion 115 (FIG. 9c) includes a transformer 550 connected to inputs 551 and 552 for coupling to an AC power line. A primary winding 553 and a primary winding 554 of transformer 550 are selectively connected in series or in parallel by relay switches 556 and 557. A secondary transformer winding 560 is connected between ground terminal 562 and an input 563 to a rectifier bridge 564. A secondary winding 561 of transformer 550 is connected between ground potential 562 and an input 565 of rectifier 564. A positive output terminal 569 of rectifier 564 is connected to an input 571 of a voltage regulator 572. An input 573 of voltage regulator 572 is connected directly to ground. A capacitor 575 is connected between input 571 and input 573. An output 574 of voltage regulator 572 is connected via the parallel connection of capacitors 576–579 to ground potential and output 580. A voltage $V_1$ is output by the AC to DC converter at output 580. Negative terminal 570 of rectifier 564 is connected to input 581 of voltage regulator 582. An input 583 of voltage regulator 582 is connected directly to ground. Input 581 is connected to ground potential via a capacitor 584. An output 583 of voltage regulator 582 is connected by the parallel connection of capacitors 586–588 to ground potential and output 583 is connected to output 589 which provides voltage potential $V_1$ therefrom.

A resistor 592 is connected between output 580 and a junction 593. A capacitor 595 is connected in series between junction 593 and ground potential, and a zener diode 594 is connected in parallel with capacitor 595 between junction 593 and ground potential. A parallel connection of a zener diode 600 and a capacitor 599 is connected between ground potential and a junction 601. A resistor 602 is connected between voltage output terminal 589 and junction 601. Accordingly, supply voltage $V_2$ is output at junction 593 and a supply voltage $V_3$ is output at junction 601.

OPERATION

In operation, when the system is powered up, a high logic level is output from ANDGATE 139 to output 138 which will be supplied to either input 130 or input 131 to place the system in manual or automatic control mode. The mode of control is changed when a high logic level is supplied to input 122 using a bounce switch (not shown) connected to input 118. When the bounce switch is closed, output 127 of data flip-flop 121 will change from a high or low logic level to a low or high logic level, respectively. When output 127 has a high logic level thereon, the system operates in an automatic control mode, and when output 127 has a low logic level thereon, the system operates in a manual control mode. When the system is in the automatic control mode, the high logic level on output 127 is input to ANDGATE 169, comparator 253 and comparator 260. Input 150 is connected to receive a video signal from camera 28. If camera 28 does not provide a video signal to the video input 150, output 156 of video detector 155 switches low, which drives output 170 of AND- GATE 169 to switch between high and low logic levels due to the oscillation input from counters. As a result, output 170 of ANDGATE 169 switches between high and low logic levels which will switch transistor 172 on and off. Accordingly, a flashing signal is applied to output 177.

Comparator 253 effectively follows output 127 of flip-flop 121. When output 127 has a high logic level thereon (+12 volts), output 252 of comparator 253 outputs a high logic level signal which is inputted to control input 243 of bilateral switch 241. Input/output 240 and input/output 242 are connected when control input 243 has a high logic level thereon. When output 127 has a low logic level thereon, comparator 253 outputs a low logic level signal and input/output 240 is isolated from input/output 242. Output 262 of comparator 260 is inverted with respect to output 127 of flip-flop 121. When output 127 has a high logic level thereon, the open collector output transistor of comparator 260 is on and the auto status lamp is connected to ground through the comparator. On the other hand, when output 127 of flip-flop 121 has a low logic level thereon, the open collector output transistor of comparator 260 is off, and automatic status indicator output 264 is not connected through this output transistor to ground.

Figure 9A:
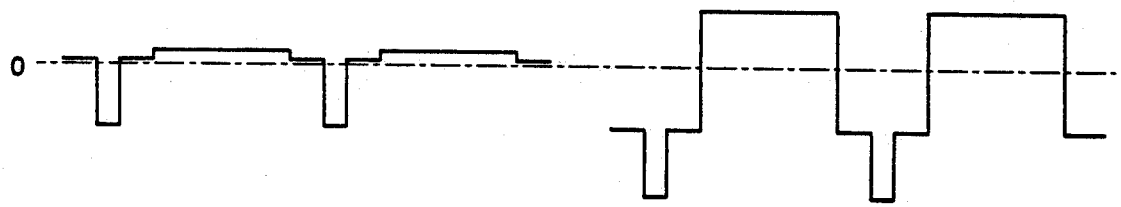
FIG. 9a is a waveform diagram of an AC video signal output to the video detector.
Figure 9B:
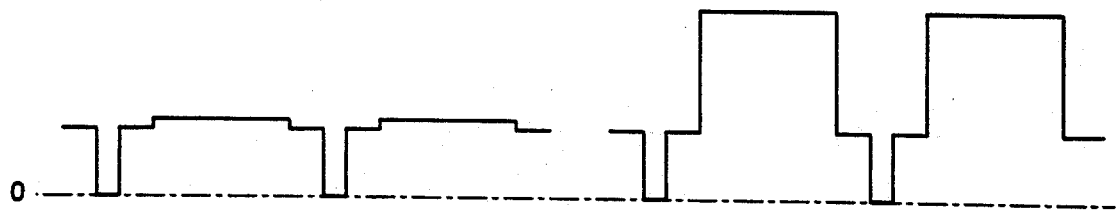
FIG. 9b is a waveform diagram of a DC video signal output from the video detector.

Video detector 107 generates an output signal at output 200 of comparator 198 responsive to the signal from camera 28 received at input 150. The signal from video camera 28, illustrated in FIG. 9a, is an AC signal comprising sync pulses. Video detector portion 107 generates a DC signal from the AC signal output from video camera 28. Circuit 107 thus comprises a comparator 181 having an open collector output, and configured as a negative peak detector. Thus when input 150 is lower than the charge on capacitor 189, the open collector output transistor of comparator 181 is on and pulls capacitor 189 lower. When input 150 is higher than the charge on capacitor 189, the open collector output transistor in comparator 181 is off and capacitor 189 holds its charge. The negative peak signal is held between sync signals from video camera 28 and is applied to the inverting input of amplifier 198. The video signal is applied to the non-inverting input of the differential amplifier 198 via voltage follower 202 and the low-pass filter formed by resistor 203 and capacitor 206. The resulting DC output signal is illustrated in FIG. 9b.

Output 200 will vary, depending on the intensity of the video signal output from camera 28 as the average level of signal 9b represents the intensity of the video signal provided to input 150. Signal 9b is not electrically averaged as the system cannot follow the rapid changes of the sync pulses and the signal is effectively averaged by the inertia of the motor. Input 223 of difference amplifier 222 receives a reference signal from reference generator 114 and the output of difference amp 224 will vary according to the difference between the signals supplied to inputs 221 and 223.

a) Automatic Control

When the system is in the automatic mode of shutter control, the output of amplifier 224 is connected to buffer 247 by bilateral switch 241 as a high logic level signal is output by amplifier 253 as described above. The signal output from amplifier 222 is thus connected to input 245 of buffer 247, the output of which is connected to input 273 of amplifier 278. Input 277 of amplifier 278 is connected to output 320 of amplifier 319. The signal output by amplifier 247 is thus differentially combined with the signal output from buffer 319, and the resulting signal magnitude output by amplifier 278 is selectively supplied to drive elements 291 and 296. Amplifier 296 supplies a drive current to the positive terminal of motor 38 to control the position of shutter 22. The negative terminal of motor 38 is selectively connected via bilateral switch 309 to a capacitor 315 which samples the signal on the negative terminal of the motor when switch 309 is closed and holds the sample when switch 309 is open. The sampled signal is input to differential amplifier 278 by a buffer amplifier 319. Bilateral switches 285 and 309 are 180° out of phase and receive a control signal such that output 279 of amplifier 278 is connected to drive amplifier 291 87.5% of the time and resistor 306 is connected to input terminal 318 of buffer 319 12.5% of the time. In this manner, output 279 of amplifier 278 is isolated from amplifiers 291 and 296, and a drive signal is not supplied to the positive terminal of motor 38 when the sample and hold capacitor 315 is connected to motor 38.

In the automatic mode of shutter control up input 355 and down input 356 are used to adjust the reference level output at junction 542 and applied to differential amplifier 222. To adjust the reference level, an operator applies a high logic level to up input 355 or to down input 356. ORGATE 380 is responsive to the up or down input signals to output a high logic level signal to ANDGATE 396. ANDGATE 396, in turn, applies a clock signal to counters 490 and 491 via ORGATE 464 and the counters count up or down depending upon the up/down inputs 495 and 499. NANDGATE 445 outputs a high logic level as input 447 is held at a low logic level. When up input 355 has a high logic level signal thereon, NANDGATE 370 generates a low logic level at output 443 and ANDGATE 441 generates a high logic level on output 453 which drives flip-flop 434 to provide a high logic level signal to inputs 495 and 499. On the other hand, when input 355 has a low logic level thereon, NANDGATE 370 has a high logic level output which is applied to NANDGATE 442, which in turn outputs a low logic level which drives flip-flop 434 to output a low logic level which is applied to inputs 495 and 499, and counters 490 and 491 count down when a clock signal is received.

Comparator 430 holds input 455 of flip-flop 434 at a low logic level when the reference potential at junction 542 is more than $V_2$. Comparator 435 provides a low logic level to NANDGATE 441 when the reference potential at output 542 drops below one diode voltage. Comparator 435 thus insures that a high logic level signal is applied to input 455 of flip-flop 434.

ANDGATE 410 outputs a timing signal which is applied to input 413 of ANDGATE 414. Input 487 of ANDGATE 410 is held high by output 127 of flip-flop 121 in the automatic mode which is connected to input 487 via ORGATE 482. The timing signal generated by ANDGATE 410 is thus continuously applied to comparators 330 and 340 when the system is in automatic shutter control mode.

b) Manual Control

When the system is in the manual mode of shutter control, output 127 of flip-flop 121 has a low logic level thereon, and amplifier 253 accordingly generates a low logic level signal which disconnects the output of amplifier 222 from buffer amplifier 247. A high logic level is generated at output 124 of flip-flop 121 and is applied to input 375 of ANDGATE 376 and input 392 of AND- GATE 391. Thus, when a positive potential is applied to input 355, a positive logic level is applied to input 375 of ANDGATE 376 and ANDGATE 376 outputs a high logic level signal which is applied to input 273 of amplifier 278. The output from amplifier 278 is selectively applied to drive amplifiers 291 and 298 which output a drive current to motor 38 which drives the shutter to a position passing more light. On the other hand, when a high logic level is applied to down input 356, a high logic level is applied to input 390 of ANDGATE 391. ANDGATE 391, in turn, outputs a high logic level to input 277 of amplifier 278. The output of amplifier 278 is selectively applied to drive amplifiers 291 and 298 which output a drive current to motor 38 which drives the shutter to a position which decreases the light applied to the target.

Input 477 of ANDGATE 475 is connected to output 124 of flip-flop 121 and receives a high logic level signal when the system is in the manual control mode. Input 476 receives a high logic level output from ORGATE 380 each time a high logic level signal is applied to input 355 or input 356. ANDGATE 475 outputs a high logic level signal each time a high logic level signal is received from ORGATE 380 while the signal is in manual mode. ORGATE 482 is connected to output 478 of ANDGATE 475 and outputs a high logic level signal each time ANDGATE 475 outputs a high logic level. ANDGATE 414 outputs a high logic level each time a clock signal is received from ANDGATE 411 while a high logic level signal is output from ORGATE 482. Comparator 340 is responsive to the output signal of ANDGATE 414 to control switch 285 to connect output 279 of amplifier 278 to input 292 of amplifier 291 when a high logic level signal is applied to input 355 or input 356. Amplifier 330 is responsive to the timing signals from ANDGATE 414 to selectively connect the negative terminal of motor 38 to capacitor 315 while a high logic level is applied to input 355 or input 356.

ANDGATE 418 is responsive to the high logic level on output 124 and clock signal from output 416 to generate a clock signal which is applied to input 463 of ANDGATE 468. ANDGATE 468 will thus provide a clock input to binary counters 490 and 491 which will cause them to increase or decrease the count on the counter according to the signal output from comparator 214 which is applied to input 455 of flip-flop 434 via NANDGATE 445. Thus, output 509 of flip-flop 434 will output a low logic level when comparator 214 outputs a low logic level signal, and flip-flop 434 will output a high logic level when comparator 214 outputs a high logic level. Up/down counters 490 and 491 will thus provide an output signal level which indicates and follows the video level when the system is in the manual control mode. The reference signals supplied to comparator 222 will thus be dependent upon the reference level established in manual mode when the system is switched from manual to automatic control.

Thus, it can be seen that a system is disclosed which provides both manual and automatic control of a shutter to adjust the amount of light applied to a target. The system includes a motor control circuit which does not require separate sensors for monitoring the amount of light supplied from a light source to the target, and provides relatively fast adjustment to changes in the amount of light reflected from the target in the automatic mode.

Changes and modifications in the specifically disclosed embodiment can be carried out without departing from the principles of the invention which are intended to be limited only by the scope of the appended claims, as interpreted according to the principles of patent law including the doctrine of equivalents.

The embodiments of the invention in which an exclusive property or privilege is claimed are defined as follows.

1. A light control system for a surgical inspective device having a camera for viewing a target and a light source for illuminating the target, comprising:
   a shutter that adjusts the amount of light supplied from the light source to the target by being positioned between the light source and the target;
   a motor operably coupled to said shutter for controlling the position of said shutter responsive to a control signal; and
   electronic means for generating said control signal, said electronic means coupled to said motor and adapted to be coupled to the camera, whereby said shutter is positioned between the light source and the target and said electronic means is coupled to an output of the camera to control the position of said shutter as a function of the output of the camera and a signal from said motor.

2. The system as defined in claim 1, wherein said motor includes a first terminal and a second terminal and said electronic means includes an output connected to said first terminal of said motor, a first input connected to said second terminal of said motor and a second input coupled to an output of said camera.

3. The system as defined in claim 2, wherein said electronic means includes a first means for switching and a second means for switching, said first means for switching including an output coupled to said first terminal of said motor and said second means for switching including an input coupled to said second terminal of said motor, 4. The system as defined in claim 3, wherein said electronic means further includes a capacitor connected to an output of said second means for switching and said second means for switching connects said capacitor to said second terminal of said motor when said first means for switching is open, and said second means for switching does not connect said capacitor to said motor when said first means for switching is closed whereby the back EMF from said motor is sampled when said electronic means is not supplying a drive signal to said motor.

5. The system as defined in claim 4, wherein said electronic means further includes an inverter and an amplifier, said inverter including an input coupled to said capacitor receive a signal level from said capacitor, said amplifier having an input connected to an output of said inverter and to a control signal input, an output of said amplifier connected to an input of said first means for switching.

6. The system as defined in claim 1, wherein said electronic means includes a video detector having an input coupled to the camera and an output selectively coupled to said motor, said video detector outputting a signal representing the intensity of the signal output by the camera.

7. The system as defined in claim 6, wherein said electronic means further includes a reference signal generator and a differential amplifier, an output of said reference signal generator coupled to one input of said differential amplifier, another input of said differential amplifier coupled to said output of said video detector.

8. The system as defined in claim 6, further including a reference signal generator, wherein an output of said video detector is coupled to an input of said reference signal generator, whereby said reference signal generator follows an output signal from said video detector when said system is responsive to manual control signals for adjusting the position of said shutter.

9. The system as defined in claim 1 further including manual control means coupled to said electronic means for manual control of the position of said shutter, said manual control means including an up input and a down input, whereby said shutter is manually controlled to pass more or less light to said target when a positive logic level signal is applied to said up or down inputs, respectively, when said system is in a manual control mode.

10. The system as defined in claim 9 wherein said up and down inputs are coupled to a reference signal generator to adjust an output signal from said reference signal generator when said system is in an automatic control mode, whereby said electronic means will automatically drive said system to an adjustable light intensity as a function of said reference signal when said system is in an automatic control mode.

11. The light control system as defined in claim 1, wherein the camera is a video camera and said electronic means further includes a video signal detector coupled to the video camera to detect the intensity of the video camera output.

12. A light control system for a camera and a light source, comprising:
a shutter positioned to vary the light supplied from said light source to a target;
a motor including a shaft coupled to said shutter, said motor controlling the position of said shutter according to a drive signal; and
electronic means for generating said drive signal, said electronic means coupled to the camera to receive a signal from said camera and including an output coupled to said motor, said electronic means including feedback means and gain establishing means, said feedback means including an input coupled to said motor and generating an output signal as a function of the shaft speed of said motor, said gain establishing means receiving said feedback means output signal and a control signal, wherein said control signal is a function of said signal from the camera whereby said shutter position is controlled as a function of said signal from the camera.

13. The system as defined in claim 12 wherein said electronic means further includes a first means for switching and said feedback means includes a second means for switching, said first means for switching including an output coupled to said motor and said second means for switching including an input coupled to said motor.

14. The system as defined in claim 12, wherein said feedback means further includes a capacitor connected to the output of said second means for switching and said second means for switching connects said capacitor to said motor when said first means for switching is open, and said second means for switching does not connect said capacitor to said motor when said first means for switching is closed whereby the back EMF from said motor is sampled when said electronic means is not supplying a drive signal to said motor.

15. The system as defined in claim 14, wherein said electronic means further includes an amplifier and said feedback means further includes an inverter, said inverter including an input coupled to receive a signal level from said capacitor and said amplifier connected to an output of said inverter and to a control signal input, and an output of said amplifier connected to an input of said first means for switching.

16. The system as defined in claim 12, wherein said electronic means includes a video detector having an input coupled to the camera and an output selectively coupled to said motor, said video detector outputting a signal representing the intensity of the signal output by the camera.

17. The system as defined in claim 16, wherein said electronic means further includes a reference signal generator, an output of said reference signal generator coupled to one input of a differential amplifier, another input of said differential amplifier coupled to said output of said video detector.

18. The system as defined in claim 16, further including a reference signal generator, and wherein said output of said video detector is coupled to an input of said reference signal generator such that said reference signal generator follows an output signal from video detector when said system is responsive to manual control signals for adjusting the position of said shutter.

19. The system as defined in claim 12 further including means for manually controlling the position of said shutter, said manual control means including an up input and a down input, whereby said shutter is manually controlled to pass more or less light to said target when a positive logic level signal is applied to said up or down inputs, respectively, when said system is in a manual control mode.

20. The system as defined in claim 19 wherein said up and down inputs are coupled to a reference signal generator to adjust an output signal from said reference signal generator when said system is in an automatic control mode whereby said electronic means will drive said system to an adjustable light intensity as a function of said reference signal when said system is in an automatic control mode.

21. The light control system as defined in claim 12, wherein the camera is a video camera and said electronic means further includes a video signal detector coupled to the video camera to detect the intensity of the video camera output.

22. A control system comprising:
a camera having an output;
a motor including a shaft coupled to a shutter, said motor responsive to a motor control signal for rotating said shaft and moving said shutter;
an input means coupled to said camera output for generating an input control signal as a function of an output signal of said camera;
a feedback means for generating a feedback signal, said feedback means including an output and a means for sampling, said means for sampling switchingly connected to said motor for sampling a signal of said motor and outputting a signal level at said sampling means output, said output of said feedback means coupled to said sampling means output; and
a drive circuit, said drive circuit responsive to said input control signal and said feedback signal for generating said motor control signal whereby the position of said shutter is controlled as a function of an output signal of said camera.

23. The system as defined in claim 22, wherein said drive circuit includes a first switch, and said sampling means includes a second switch, said first switch including an output coupled to said motor and said second switch including an input coupled to said motor.

24. The system as defined in claim 23, further including a capacitor coupled to said second switch wherein said second switch connects said capacitor to said motor when said first switch is open, and said second switch does not connect said capacitor to said motor when said first switch is closed whereby said capacitor samples the back EMF of said motor when said first switch is open such that the back EMF from said motor is sampled when said electronic means is not supplying a drive signal to said motor.

25. The system as defined in claim 24, wherein said feedback means further includes an inverter, said inverter including an input coupled to said capacitor to receive a signal level from said capacitor, and said drive circuit including an amplifier coupled to said input means and to an output of said inverter, and wherein an output of said amplifier is connected to said first switch.

26. The light control system as defined in claim 22, wherein the camera is a video camera and said electronic means further includes a video signal detector coupled to the video camera to detect the intensity of the video camera output.

* * * * *

UNITED STATES PATENT AND TRADEMARK OFFICE
CERTIFICATE OF CORRECTION

PATENT NO. : 5,272,426
DATED : December 21, 1993
INVENTOR(S) : James C. Cook, II It is certified that error appears in the above-indentified patent and that said Letters Patent is hereby corrected as shown below:

Column 2, line 66;
"output" should be -- input --;

Column 3, line 59;
"$\theta_m$" should be -- $\dot{\theta}_m$ --;

Column 3, line 68;
"$\theta_s$" should be -- $\Theta_s$ --;

Column 5, line 4;
"Striction" should be -- Stiction --;

Column 14, line 34;
"$V_1$" should be -- $V_4$ --;

Column 18, line 37, claim 3;
"motor," should be -- motor. --;

Column 19, line 59, claim 14;
"claim 12" should be -- claim 13 --.

Signed and Sealed this

Sixteenth Day of August, 1994

Attest:

BRUCE LEHMAN

Attesting Officer

Commissioner of Patents and Trademarks